United States Patent [19]

Flagler

[11] Patent Number: 5,155,624
[45] Date of Patent: Oct. 13, 1992

[54] LENS HOUSING FOR STERILE COVER OF AN OPERATING MICROSCOPE

[75] Inventor: Robert W. Flagler, Collierville, Tenn.

[73] Assignee: Smith & Nephew Richards, Inc., Memphis, Tenn.

[21] Appl. No.: 543,152

[22] Filed: Jun. 25, 1990

[51] Int. Cl.$^5$ .................. B65D 85/38; G02B 27/00
[52] U.S. Cl. .................................... 359/510; 359/511
[58] Field of Search .............. 350/585, 587, 318, 319; 359/507, 510, 511, 592, 894

[56] References Cited

U.S. PATENT DOCUMENTS

| | | | |
|---|---|---|---|
| 3,528,720 | 9/1970 | Treace | 350/585 |
| 3,698,791 | 10/1972 | Walchle et al. | 350/585 |
| 3,796,477 | 3/1974 | Geraci | 350/587 |
| 4,385,812 | 5/1983 | Wille et al. | 350/587 |
| 4,561,540 | 12/1985 | Hunter et al. | 350/587 |
| 4,564,270 | 1/1986 | Willie | 350/587 |

*Primary Examiner*—Bruce Y. Arnold
*Assistant Examiner*—R. D. Shafer
*Attorney, Agent, or Firm*—Pravel, Gambrell, Hewitt, Kimball & Krieger

[57] ABSTRACT

A lens housing and cover for a disposable microscope drape including a housing formed of a flexible, easily distortable, resilient material adapted to be connected to a disposable microscope drape and positioned adjacent to an objective lens of an operating room microscope. The housing includes an opening for registering with the objective lens. A lens cover includes an optically clear portion for spanning the opening and a gripping portion projecting from the optically clear portion and from the housing when the lens cover is in the housing. The housing further includes a wall defining said opening, the wall including an elongated slot through which the lens cover can be inserted gripping portion can be inserted for installing the cover end through which the cover can be removed by pulling on the gripping portion, the elongated dimension of the slot being smaller than at least one portion of the dimension of the lens cover which spans the opening so that the housing has to be distorted for the lens cover to be inserted and removed. The portion of the wall defining the opening is aligned with the slot and includes two pairs of spaced ridges for holding the lens cover in place after it has been inserted through the slot.

7 Claims, 1 Drawing Sheet

LENS HOUSING FOR STERILE COVER OF AN OPERATING MICROSCOPE

BACKGROUND OF THE INVENTION

This invention relates to a sterilizable, disposable lens housing and associated lens cover for the objective lens ring of an operating microscope and, in particular, to an improved structure of the housing and lens cover carried by the housing.

For many types of operations which involve the use of microsurgical techniques, an operating room microscope is used so that the physician can easily observe all of the elements in the surgical field. In order to maintain the sterility of all of the elements within the surgical field, disposable sterilized drapes are used for covering the microscope.

In order to prevent any distortion of images observed by the operating physician, optically clear lens covers have been developed for connection to the removable drape prior to the operation. Because certain types of surgical operations result in bone fragments and/or blood being splattered on the lens cover, it is important to have a lens cover and housing where the lens cover can easily be removed and replaced, if desired, so that the surgeon can have a clear and unobstructed view of the surgical field.

One lens housing and cover generally of the type described is the subject of U.S. Pat. No. 3,796,477 where a housing formed of a flexible, easily distortable resilient material such as 70 durometer PVC is described. In that patent, an annular housing with a groove along its entire inner surface is designed to receive a lens cover which fits within the groove. The cover has a tab portion designed to fit within a slot formed in the outer surface of the ring. Although this ring has been used over the years, it has the disadvantage of having a lens cover that is somewhat difficult to insert into the annular ring because the cover must be inserted with the leading edge first placed in the groove and then the tab pushed down into the slot.

Another type of lens housing is shown in U.S. Pat. No. 4,564,270 where a housing with a laminated structure is provided to be used with a lens cover that is slidable into a U-shaped slot formed between two adjacent portions. The slot is generally equal in size to the lens cover which is inserted. The perimeter of the lens is formed with a roughened surface which is said to maintain the lens cover within the slot of the housing which is not considered to be a sufficient way for holding the lens in the slot. Furthermore, since the thickness of the slot within which the lens cover is inserted is equal to the width of the cover, so that if blood or other debris is splattered on the cover and the cover is removed the debris will be deposited and spread along the adjacent surface. This either results in an accumulation of the debris or causes the debris to be redeposited on a replacement lens cover if one is re-inserted into the holder.

SUMMARY OF THE INVENTION

The invention described in detail solves the problems described above by providing a lens housing for disposable microscope drapes which can be easily positioned and firmly held in an annular housing where any blood or other debris is not deposited on the housing when the lens cover is removed.

In accordance with the invention, a housing is provided which is formed of a flexible, easily distortable, resilient material adapted to be connected to a disposable microscope drape and positioned adjacent to an objective lens of an operating microscope. The housing includes an opening which registers with the objective lens.

A lens cover which includes an optically clear portion for spanning the opening also includes a gripping portion projecting from the optically clear portion and from the housing when the lens cover is in the housing.

The housing includes a wall defining the opening which includes an elongated slot through which the handle portion of the lens cover is first inserted, the elongated dimension of the slot being smaller than at least one portion of the dimension of the lens cover which spans the opening. The handle is grasped and pulled slightly through the slot so that the housing has to be distorted for the lens cover to be seated in two pairs of spaced holding ridges or similar structure formed on the portion of the wall defining the opening in a line with the slot for holding the lens cover in place. These ridges can be located on either side of the center line of the direction of insertion of the lens cover.

The housing is preferably an annular ring which is molded from a single piece of a flexible, easily distortable and resilient material such as a thermoplastic rubber, for example, KRATON sold by Shell Oil Company, or a silicone rubber. The lens cover is preferably a single piece of optically clear plastic with a gripping portion formed integral with the optically clear portion.

The annular ring has an inner diameter which is substantially the same as that of the lens cover, with the slot in the housing extending around less than half the circumference of the ring so that the ring must be distorted in order to insert and remove the lens cover. This provides a snug fit for the lens cover for holding it firmly in place.

The slot is wide enough to accommodate the lens cover easily and is formed with a pair of projections on the outer surface side of the slot. These projections operate to space the inner defining surface of the slot from the lens cover as the lens cover is being removed or inserted in place. This prevents any blood or other debris on the surface of the lens cover from wiping onto the surface defining the slot so that the objective lens cover can be removed from the ring and replaced with a new sterile lens without having the blood or debris accumulate on the housing or be redeposited on the replacement lens cover.

BRIEF DESCRIPTION OF THE DRAWINGS

A better understanding of the invention can be obtained from the detailed description of the invention set forth below when it is considered in conjunction with the drawings, in which.

DETAILED DESCRIPTION OF A PREFERRED EMBODIMENT

Figure 1:
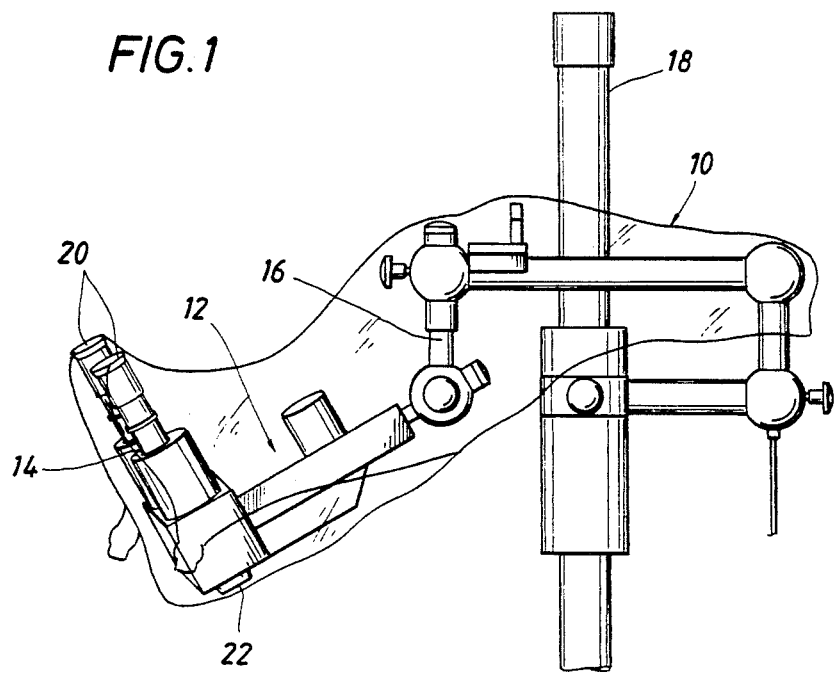
FIG. 1 is a perspective view of an operating room microscope showing a disposable, sterilized drape in combination with the lens housing of the present invention.

FIG. 1 illustrates a surgical drape 10 mounted on an operating room microscope generally designed by reference numeral 12 which includes a head unit 14 supported on a succession of cantilevered arms 16 which are connected to a floor-mounted column 18. The microscope 14 includes a pair of binocular viewing oculars 20 which are opposite an objective lens (not shown) over which a lens housing 22 of the present invention is mounted.

Figure 2:
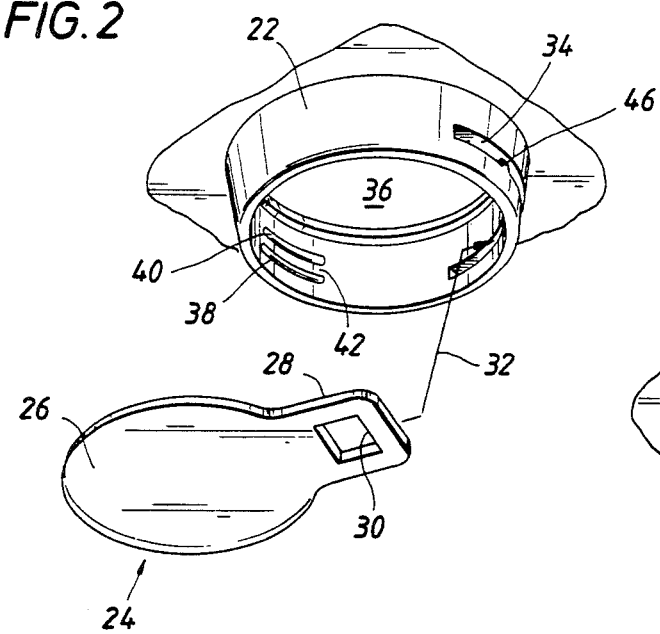
FIG. 2 is a perspective view of the lens housing formed in accordance with the invention with the lens cover in position to be inserted into the housing.

Referring to FIG. 2, the housing 22 is preferably annular in shape and for the reasons described below is formed of a flexible, easily distortable, resilient material. While any number of materials could be used which can be sterilized, molded thermoplastic rubber such as KRATON sold by Shell Oil Company is preferred. Silicone rubber could also be used. As shown, the housing 22 is designed to receive a lens cover 24 which is preferably formed of single piece of optically clear plastic that includes a viewing portion 26 and a gripping portion 28 or handle with an opening 30 for easy handling by the operator.

As indicated by arrow 32 in FIG. 2, the lens cover 24 is inserted into the housing 22 by first inserting the gripping portion or handle 28 through a slot 34 formed in the wall of the housing 22 which also defines an opening 36 which registers with the objective lens of the microscope 14. The diameter of the optically clear portion 26 of the lens cover 24 is substantially the same as the diameter of the opening 36. However, the slot 34 extends around less than half of the circumference of the wall which defines the opening 36, and, accordingly, is smaller than the diameter of the optically clear portion 26. This means that when the lens cover 24 gripping portion 28 is inserted into the slot 34 in the direction of the arrow 32 and pulled by the user, the annular housing 22 must be distorted. In this way, when the lens cover 24 is fully inserted as described below, it is held firmly in place and requires an operator pulling on it and distorting the housing 22 to remove the lens cover 24 through the slot 34.

Figure 3:
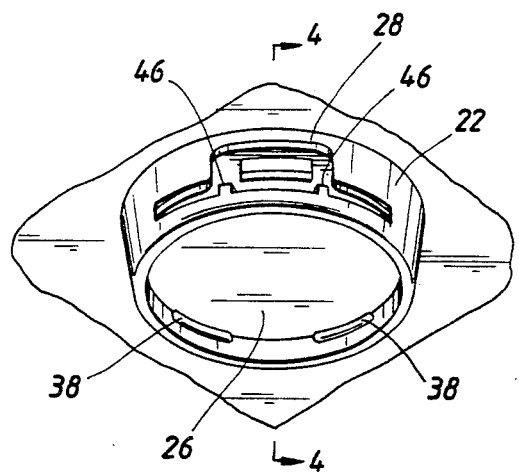
FIG. 3 is a perspective view rotated 90° from the one in FIG. 2 showing the lens cover in place in the housing.

As shown best in FIGS. 2 and 3, two pairs of ridges 38 and 40 are formed on the inner wall surface of the housing 22 which defines the opening 36. Each pair forms a space 42 between them for receiving the edge of the optically clear portion 26 of the lens cover 24. A pair of these ridges 38, 40 are formed on each side of the center line of the housing 22 as shown in FIG. 3 so that the spaces 42 are aligned with the slot 34 for holding the lens cover in the position shown in FIG. 3.

In order to install the lens cover 24, the handle 28 is first inserted through the slot 34 and pulled through the slightly distorted housing 22 until the edge is aligned with the spaces 42 and then pushed into place. In order to remove the lens cover 24, the handle 28 is grasped and the cover is pulled through the slot 34, which is possible because of the distortability of the housing 22.

As shown best in FIG. 3, a pair of spacers in the form of projections 46 are formed on the surface defining the slot 34 which engages the outer surface of the lens cover 24. These projections 46 maintain a space between the lens cover 24 and that adjacent surface. The projections 46 are provided so that if blood or other debris is deposited on the outer surface of the lens cover 24, the lens cover 24 can be removed by being pulled back through the slot 34 as described so that the lens cover 34 can be removed and replaced, if desired, by a clean, sterile cover.

By maintaining a space between the outer surface of the lens cover 24 and the surface which defines the slot 34, the blood and debris will not accumulate on the housing or be deposited or wiped on the lens cover 24 so that when the lens cover 24 is replaced it will not have the blood or other debris wiped onto it. In this way, the lens cover can easily be replaced without dirtying the lens cover once again and obstructing the surgeon's field of view.

Figure 4:
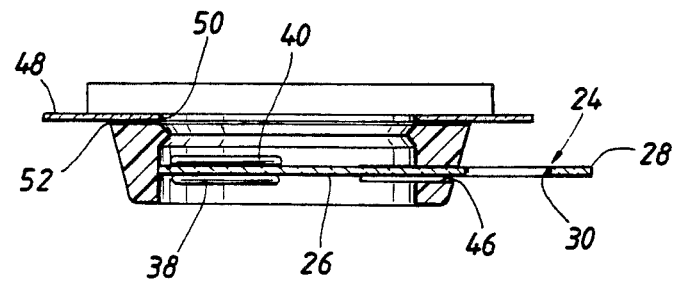
FIG. 4 is a sectional view of the lens cover and housing of the present invention looking along the line 4—4 shown in FIG. 3.

As shown best in FIG. 4, the disposable drape 10 can be formed with a support ring 48 around an opening 50 designed to fit around the objective lens portion of the microscope 14. The ring 48 can be heat sealed onto the drape or, alternatively, as shown in FIG. 4, the ring 48 can be coated with a pressure sensitive adhesive 52 so that the housing 22 can easily be attached to the ring 48.

The invention described in detail above is believed to solve the problems of the prior art because a lens cover is provided with an annular housing where the cover can easily be inserted and registered with projections formed on the inner surface of the housing and held firmly in place. If blood or other debris is deposited on the outer surface of the lens cover, the cover can easily be removed and replaced without any of the blood or other debris being re-deposited on the cover.

It should be understood that a preferred embodiment of the invention has been described and illustrated and that many variations or improvements can be made without departing from the spirit and scope of the invention and that all such variations and improvements are contemplated as falling within the scope of the following claims.

I claim:

1. A lens housing and cover for a disposable microscope drape, comprising:
   a housing formed of a flexible, easily distortable, resilient material;
   means for connecting the housing to a disposable microscope drape so that the housing is positioned adjacent to an objective lens of a microscope;
   the housing including an opening for registering with the objective lens;
   a lens cover including an optically clear portion for spanning the opening and a gripping portion projecting from the optically clear portion and from the housing when the lens cover is in the housing, the lens cover including a side facing the microscope and a side facing away from the microscope;
   the housing further including a wall defining said opening, the wall including wall surfaces having an elongated slot, said elongated slot having an inner defining surface through which the lens cover can be inserted and/or removed, the elongated dimension of the slot being smaller than at least one portion of the dimension of the lens cover which spans the opening so that the housing has to be distorted for said one portion of the lens cover to be moved through the slot;
   holding means on the portion of the wall defining said opening aligned with the slot for holding the lens cover in place after it has been inserted through the slot;

spacing means for spacing the side of the lens cover facing away from the microscope from the inner defining surface of the elongated slot as the lens cover is withdrawn through the slot, said spacing means including projection means formed on said inner defining surface of the slot for providing point engagement with the lens cover for preventing debris on the cover from wiping off on said inner defining surface.

2. The housing and cover of claim 1, wherein said housing and cover are annular in shape.

3. The housing and cover of claim 1, wherein the housing is molded into a single piece of thermoplastic rubber.

4. The housing and cover of claim 1, wherein the lens cover and gripping portion is formed of a single piece of optically-clear plastic.

5. The housing and cover of claim 1, wherein the housing defines an annular opening and the lens cover has a diameter substantially the same as the diameter of the opening, the slot extending around the housing is less than half the circumference of the spring.

6. The housing and cover of claim 1, wherein the holding means includes two pairs of upper and lower ridges, with a space in between, one pair on either side of the center line of insertion of the cover.

7. The lens housing and cover of claim 1, wherein the means for spacing includes a pair of projections on the inner defining surface of the slot for providing point engagement with the cover.

* * * * *